United States Patent [19]

Engel et al.

[11] Patent Number: 4,841,047
[45] Date of Patent: Jun. 20, 1989

[54] 4-BENZYL-1-(2H)-PHTHALAZINONE-DERIVATES

[75] Inventors: Jürgen Engel, Alzenau; Gerhard Scheffler, Hanau, both of Fed. Rep. of Germany

[73] Assignee: Aasta Pharma AG, Frankfurt, Fed. Rep. of Germany

[21] Appl. No.: 928,458

[22] Filed: Nov. 10, 1986

[30] Foreign Application Priority Data

Nov. 11, 1985 [DE] Fed. Rep. of Germany ....... 3539873

[51] Int. Cl.$^4$ .................... A61K 31/50; A61K 31/55; C07D 403/04; C07D 401/04
[52] U.S. Cl. .................................. 540/599; 544/235; 544/237; 514/212; 514/248
[58] Field of Search ................ 540/599; 544/235, 237

[56] References Cited

U.S. PATENT DOCUMENTS 3,017,411 11/1962 Engelbrecht .................. 840/599
3,813,384 5/1974 Volgelsang et al. ............ 50/599

FOREIGN PATENT DOCUMENTS 0174464 3/1986 European Pat. Off. ......... 540/599
2114884 10/1972 Fed. Rep. of Germany ...... 540/599
3530793 3/1986 Fed. Rep. of Germany ...... 540/599

OTHER PUBLICATIONS

Tatsumi et al, "Japan J. Pharmacol.", vol. 30, pp. 37–48 (1980).
Chemical Abstracts, vol. 92 (1980), Item 191057f abstracting Tatsumi et al., above.
Chem. Abstracts, vol. 81, 1974, p. 63654.

Primary Examiner—Robert T. Bond
Attorney, Agent, or Firm—Cushman, Darby & Cushman

[57] ABSTRACT

There are provided 4-benzyl-1-(2H)-phthalazinone derivatives having antiallergic activity of the formula

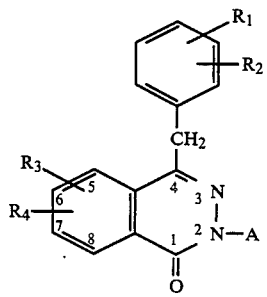

wherein $R_1$ represents fluorine, chlorine, bromine, trifluoromethyl, $C_1$-$C_6$-alkyl, hydroxy, $C_1$-$C_6$-alkoxy, $C_2$-$C_6$-alkanoyloxy, amino, $C_1$-$C_6$-alkylamino, di-$C_1$-$C_6$-alkylamino, $C_2$-$C_6$-alkanoylamino, $C_2$-$C_6$-alkanoyl-$C_1$-$C_6$-alkylamino or a nitro group, $R_2$ represents hydrogen or has one of the meanings given for $R_1$, whereby $R_1$ and $R_2$ may be the same or different, the radicals $R_3$ and $R_4$ are the same or different and represent hydrogen, halogen, $C_1$-$C_6$-alkyl, hydroxy, $C_1$-$C_6$-alkoxy, benzyloxy or $C_2$-$C_6$-alkanoyloxy and A represents an azacycloalkanyl radical, the aza nitrogen of which contains a $C_1$-$C_6$-alkyl group which is substituted by various radicals, and processes for their manufacture.

8 Claims, No Drawings

4-BENZYL-1-(2H)-PHTHALAZINONE-DERIVATES

BACKGROUND OF THE INVENTION

In German patent specification No. 21 64 058 and related Vogelsang U.S. Pat. No. 3,813,384 (the entire disclosure of which is hereby incorporated by reference and relied upon) there are disclosed basic substituted 4-benzyl-1-(2H)-phthalazinone derivatives of the following formula

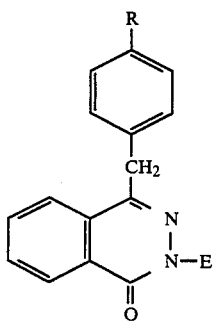

wherein R represents hydrogen or a halogen atom, a trifluoromethyl group or a lower alkyl or alkoxy group and E represents a 4-perhydroazepinyl, N-methyl-4-perhydroazepinyl, 3-quinuclidinyl, 3-tropanyl, 3-nortropanyl, N-methyl-3-pyrrolidinyl or N-methyl-2-pyrrolidinyl-methyl radical as well as physiologically acceptable acid addition salts thereof.

These compounds possess antihistamine activity.

SUMMARY OF THE INVENTION

The invention is directed to 4-benzyl-1-(2H)-phthalazinone derivatives of the formula

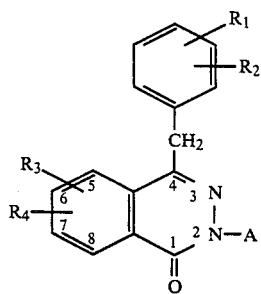

wherein $R_1$ represents fluorine, chlorine, bromine, trifluoromethyl, $C_1$-$C_6$-alkyl, hydroxy, $C_1$-$C_6$-alkoxy, $C_2$-$C_6$-alkanoyloxy, amino, $C_1$-$C_6$-alkylamino, di-$C_1$-$C_6$-alkylamino, $C_2$-$C_6$-alkanoylamino, $C_2$-$C_6$-alkanoyl-$C_1$-$C_6$-alkylamino or a nitro group, $R_2$ represents hydrogen or has one of the meanings given above for $R_1$, whereby $R_1$ and $R_2$ may be the same or different, $R_3$ and $R_4$ may be the same or different and represent hydrogen, halogen, $C_1$-$C_6$-alkyl, hydroxy, $C_1$-$C_6$-alkoxy, benzyloxy or $C_2$-$C_6$-alkanoyloxy and A represents one of the radicals

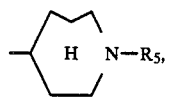

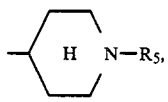

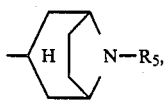

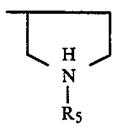

or

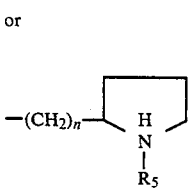

wherein n=1 or 2 and $R_5$ represents a $C_1$-$C_6$-alkyl group substituted by the following radicals:

(a) by a phenyl radical or a phenyl carbonyl radical each of which may contain one, two or three substituents, which may be the same or different, whereby the substituents are halogen atoms, trifluoromethyl, $C_1$-$C_6$-alkyl groups or $C_1$-$C_6$-alkoxy groups, or (b) by a $C_1$-$C_6$-alkoxy radical, a mono or dihydroxy-$C_1$-$C_6$-alkyl radical or a hydroxy-$C_1$-$C_6$-alkoxy radical or (c) by a mono-$C_1$-$C_6$-alkylamino or di-$C_1$-$C_6$-alkylamino radical whereby the latter may also be closed to form a 5–7 membered, nitrogen-containing ring, which may optionally contain a further oxygen atom, or (d) by a $C_3$-$C_8$-cycloalkyl radical or a $C_3$-$C_8$-cycloalkylcarbonyl radical or whereby $R_5$ is a monounsaturated $C_3$-$C_6$-alkyl group, a monounsaturated $C_3$-$C_6$-alkyl group with a phenyl radical, a monounsaturated $C_3$-$C_6$-alkylcarbonyl group or a monounsaturated $C_3$-$C_6$-alkylcarbonyl group with a phenyl radical and physiologically acceptable acid addition salts thereof, with the exception of the compounds wherein A represents the radical

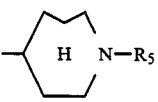

and $R_5$ represent allyl, benzyl, phenylethyl or methoxyethyl, $R_1$ represents chlorine in the 4-position and $R_2$, $R_3$ and $R_4$ represent hydrogen.

The invention also includes a process for the preparation of 4-benzyl-1-(2H)-phthalazinone derivatives of the formula

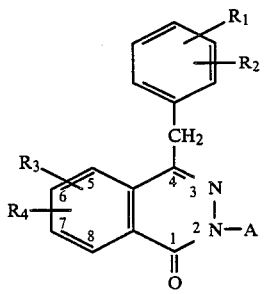

wherein $R_1$ represents fluorine, chlorine, bromine, trifluoromethyl, $C_1$-$C_6$-alkyl, hydroxy, $C_1$-$C_6$-alkoxy, $C_2$-$C_6$-alkanoyloxy, amino, $C_1$-$C_6$-alkylamino, di-$C_1$-$C_6$-alkylamino, $C_2$-$C_6$-alkanoylamino, $C_2$-$C_6$-alkanoyl-$C_1$-$C_6$-alkylamino or a nitro group, $R_2$ represents hydrogen or has one of the meanings given above for $R_1$ whereby $R_1$ and $R_2$ may be the same or different, the radicals $R_3$ and $R_4$ may be the same or different and represent hydrogen, halogen, $C_1$-$C_6$-alkyl, hydroxy, $C_1$-$C_6$-alkoxy, benzyloxy or $C_2$-$C_6$-alkanoyloxy and A represents one of the radicals

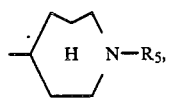

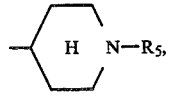

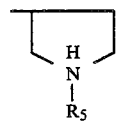

or

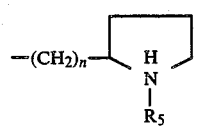

wherein $n=1$ or 2, whereby $R_5$ represents a $C_1$-$C_6$-alkyl group substitued by the following radicals:

(a) by a phenyl radical or a phenyl carbonyl radical each of which may contain one, two or three substituents, which may be the same or different, whereby the substituents are halogen atoms, trifluoromethyl, $C_1$-$C_6$-alkyl groups or $C_1$-$C_6$-alkoxy groups, or (b) by a $C_1$-$C_6$-alkoxy radical, a mono or dihydroxy-$C_1$-$C_6$-alkyl radical or a hydroxy-$C_1$-$C_6$-alkoxy radical or (c) by a mono-$C_1$-$C_6$-alkylamino or di-$C_1$-$C_6$-alkylamino radical whereby the latter may also be closed to form a 5–7 membered, nitrogen-containing ring, which may optionally contain a further oxygen atom, or (d) by a $C_3$-$C_8$-cycloalkyl radical or a $C_3$-$C_8$-cycloalkylcarbonyl radical or whereby $R_5$ is a monounsaturated $C_3$-$C_6$-alkyl group, a monosaturated $C_3$-$C_6$-alkyl group with a phenyl radical, a monounsaturated $C_3$-$C_6$-alkylcarbonyl group or a monounsaturated $C_3$-$C_6$-alkylcarbonyl group with a phenyl radical and physiologically acceptable acid addition salts thereof, with the exception of compounds where A represents the radical

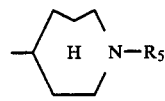

and $R_5$ represents allyl, benzyl, phenylethyl or methoxyethyl, $R_1$ represents chlorine in the 4-position and $R_2$, $R_3$ and $R_4$ represent hydrogen characterized in that (a) a compound of the formula

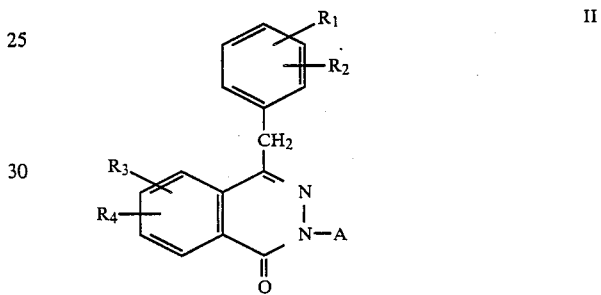

II wherein $R_1$, $R_2$, $R_3$, $R_4$ and A have the meanings given above and $R_5$ represents hydrogen, is reacted with a compound of the formula $R_5X$   III wherein $R_5$ has the meaning given above and X is a hydroxy group esterified with a strong inorganic or organic acid or (b) a compound of the formula

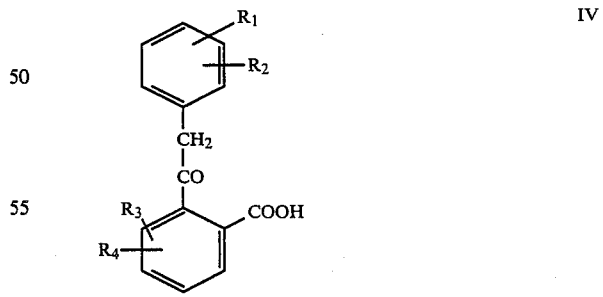

IV or a functional derivative thereof, wherein $R_1$, $R_2$, $R_3$ and $R_4$ have the meanings given above, is reacted with a hydrazine of the general formula $H_2N-NH-Z$   V wherein Z represents hydrogen or the radical A, and A has the meaning given above; and where Z represents hydrogen, the benzylphthalazinone derivatives so obtained are subsequently reacted with a compound of the formula

Y—A   VI wherein Y represents a halogen atom or a sulfonic acid ester group and A has one of the meanings given above, the so obtained compound is, if desired, alkylated or acylated to introduce a $C_1$-$C_6$-alkyl group, a benzyl group and/or a $C_2$-$C_6$-alkanoyl group and/or acyl group which may be present are split off and if desired the so obtained compounds are converted into acid addition salts thereof.

The compounds of formula I are used as therapeutically active ingredients. The compounds of the general formula I are used in medicaments in association with conventional carriers and/or diluents or auxiliary agents.

Medicaments can be prepared by a process characterized in that a compound of the general formula I is brought into a therapeutically acceptable form together with conventional pharmaceutical carriers and/or diluents or other auxiliary agents to give pharmaceutical formulations or to yield a therapeutically acceptable formulation.

The compounds of the general formula I can be used in the preparation of medicaments.

The compounds according to the present invention possess antiallergic, histaminolytic and asthma prophylactic activity, but are, however, considerably stronger and better than the compounds known from German patent specification No. 21 64 058 and the corresponding Volgelsang U.S. Patent. In addition, in contradistinction to the known medicament AZELASTIN (the compound according to example 5 of German patent specification No. 21 64 058 and the Vogelsang) they do not have any, or at least no considerable, bitter taste so that they can without any difficulty for example also be used in the form of an aerosol. In addition, the compounds of the present invention also possess analgesic activity, in particular peripheral analgesic activity. This analgesic activity is demonstrated, for example, by the Randall-Selito Test on rats (inflammation pain in rats).

The radical $R_1$ is preferably in the 4-position of the phenyl ring; the radical $R_2$ preferably in the 3-position. $C_1$-$C_6$-alkyl groups, $C_1$-$C_6$-alkoxy groups or alkanoyl groups (for example $C_2$-$C_6$-alkanoyloxy groups) may be straight or branched chain, such radicals may, in particular, contain from 1-4 or 2-4 carbon atoms.

The radicals $R_3$ and $R_4$ may be situated in the 5-, 6-, 7- and 8-positions of the 1-(2H)-phthalazinone radical, preferably in the 6- and or 7-positions.

If $R_5$ represents a $C_1$-$C_6$-alkyl group which is substituted by the given radicals, $R_5$ preferably contains one, two or three carbon atoms whereby the substituent is then preferably in the ω-position.

Especially favorable activity is possessed for example by these compounds where the groups $R_1$ to $R_4$, A and $R_5$ have the following meanings: $R_2$, $R_3$ and $R_4$=hydrogen; $R_1$=fluorine, chlorine or bromine, especially in the position, preferably fluorine in the position; A=the hexahydroazepin-4-yl-group or the piperidyl-(4)-group; $R_5$=a $C_1$-$C_6$-alkyl group (preferably methyl, ethyl, propyl, isopropyl), which contains in the ω-position an unsubstituted or substituted phenyl group or phenylcarbonyl group. The substituents of this phenyl group or phenylcarbonyl group can be for example a $C_1$-$C_4$-alkyl group (especially methyl) or a halogen (for example Cl, F) or a $CF_3$- group in the 3-position, or three $C_1$-$C_4$-alkoxy groups (especially methoxy groups) in the 3,4- and 5-position.

In the event the phenyl group or the phenylcarbonyl group contains no substituents, $R_1$ is preferably fluorine in the 4-position, $R_2$, $R_3$ and $R_4$ hydrogen, A a piperidyl-(4)- or preferably hexahydroazepin-4-yl and $R_5$ phenylmethyl, phenylethyl, 3-phenyl-propyl or 2-phenyl-propyl-(1) or phenylcarbonylmethyl.

PROCESS (A)

The process can be carried out without any additional solvent or in a suitable solvent or dispersing agent. Solvents or dispersing agents which may be used include for example: aromatic hydrocarbons such as, for example, benzene, mesitylene, toluene, xylene; pyridine; lower aliphatic ketones such as, for example, acetone, methylethylketone, halogenated hydrocarbons such as, for example, chloroform, 1,2-dichloroethane, tetrachloromethane, chlorobenzene, methylene chloride; ethers such as, for example, tetrahydrofuran, dioxane, diisopropyl ether; sulphoxides such as, for example, dimethylsulphoxide; tertiary acid amides such as, for example, dimethylformamide, dimethylacetamide, hexamethylphosphoric acid triamide, tetramethyl urea, N-methyl pyrrolidone; lower alcohols such as, for example, methanol, ethanol, isopropanol, amyl alcohol, butanol, tertiary butanol as well as mixtures thereof. The reaction may, for example, be carried out at temperatures between 20° and 200° C., preferably 40° to 160° or also 50° to 120°. Where a solvent or a dispersing agent is used, the reaction is often carried out at the reflux temperature thereof. The reaction often already takes place at room temperature or at a temperature between 40° and 120° C.

The reaction is preferably carried out in the presence of acid binding agents such as an alkali carbonates, potash, soda, alkali acetates, alkali hydroxides or tertiary bases (triethylamine, pyridine).

Where X represents an esterified hydroxy group, then this may be considered to be a functional ester. A functional ester which may be used, for example, is one with a strong organic or inorganic acid, but especially a hydrohalic acid, for example a hydrochloric, hydrobromic or hydroiodic acid or a sulphonic acid such as an aryl or $C_1$-$C_6$-alkylsulphonic acid, for example a lower alkylbenzene sulphonic acid (p-toluenesulphonic acid). Solvents which may be used include, in particular, solvents such as dioxane/water, dimethylformamide/water or lower saturated aliphatic alcohols.

Novel starting materials of formula III may be prepared by methods analogous to *Houben-Weyl, Methods in Organic Chemistry* (Methoden der Organischen Chemi) Volume 5/3 (1962), pages 503 et seq, volume 6/2 (1963), pages 475 et seq. or volume 9 (1955), page 426.

The preparation of starting materials of formula II:

The starting material of formula II wherein $R_1$ represents fluorine in the 4-position, $R_2$ represents hydrogen and A represents a 4-piperidyl radical may for example be prepared as follows:

N-Benzoyl-N'-(N-methyl-piperidin-4-yl)-hydrazine 272 g (2 mol) of benzoic acid hydrazide are added to 1500 ml of methanol with stirring. Over 1 hour, 226 g (2 mol) of 1-methyl-4-piperidinone are then added dropwise at a temperature of 30° C. Slight cooling is necessary. The reaction mixture is stirred for half an hour at 30° C. and then for a further 1 hour at 60° C. The solution is then cooled to 0° C. and over a period of 2 hours 68 g (1.8 mol) NaBH$_4$ is added using a spatula (strong foaming)..Towards the end of the addition the mixture is warmed to room temperature. The solvent is evaporated off using a rotary evaporator and to the residue 900 g ice and 1000 ml dichloromethane are added with stirring. The organic phase is separated using a separating funnel and the aqueous phase is shaken twice with 300 ml dichloromethane in each case. The combined organic fractions are dried over MgSO$_4$, the dichloromethane evaporated off and the residue recrystallized in 1 liter of isopropanol with the addition of 10 g active charcoal. The reaction product is dried in a drying cupboard at 50° C. in vacuo. (M.p. 149°–150° C.).

4-Hydrazino-N-methylpiperidine×2 HCl.

700 ml of 37% HCl (8.4 mol) are added to 400 ml water, 233 g (1 mol) N-benzoyl-N'-(N-methylpiperidin-4-yl)-hydrazine are then added with stirring and the reaction mixture refluxed for 2 hours. The liberated benzoic acid crystallizes out. It is cooled in an ice bath and suction filtered. The filtrate is evaporated on a rotary evaporator. In order to remove any water present, 250 ml methanol are added and distilled off again. By stirring the oily substance in 300 ml methanol a crystalline product is obtained which is suction filtered, washed with methanol and dried under vacuum at 50° C. (M.p. 173° C.).

2-(4-Fluorophenacetyl)-benzoic acid

A solution of 410 ml 29% NaOH is heated to a temperature of 70° C. using an oil bath and 250 g (1.04 mol) of 4-fluorobenzylidenephthalide added with stirring. Towards the end of the addition the oil bath temperature is raised to move. During the reaction a red oil is formed. After 3 hours the mixture is cooled, 500 ml of ice water are added and 340 ml of concentrated hydrochloric acid dropwise. Pink crystals separate out. These are suction filtered and washed with chloride-free ice water. After drying at 50° C. recrystallization from 900 ml toluene is carried out. (M.p. 147°–150' C.).

4-(4-Fluorobenzyl)-2-(N-methylpiperidin-4-yl)-1-(2H)-phthalazine 112.3 g 85% KOH (1.7 mol) are dissolved in 1890 ml methanol with stirring. 214 g (0.945 mol) 4-hydrazino-N-methylpiperidine×2 HCl are added and the base liberated. The resulting KCl crystallizes out. After addition of 244 g (0.945 mol) 2-(4-fluorophenacetyl)-benzoate the mixture is stirred under reflux over a period of 4 hours (in the case of other hydrazine compounds and/or phenacetylbenzoate this conversion may take somewhat longer, for example up to 20 hours). After cooling the KCl is separated off and the solution reduced on a rotary evaporator, 1000 ml ice water and 928 ml NaOH (twice molar) are added with stirring. The N-methyl compound separates out and is suction filtered, washed with ice water and dried in a drying cupboard at 50° C. under vacuum. (M.p. 140°–143° C.).

4-(4-Fluorobenzyl)-2-(N-carbethoxy-piperidin-4-yl)-1-(2H)-phthalazinone 366.5 g (1.043 mol) 4-(4-Fluorobenzyl)-2-(N-methylpiperidin-4-yl)-1-(2H)-phtalazinone are dissolved in 1100 ml toluene which had been dried over K$_2$CO$_3$. Any water present in azeotropically distilled off using a water separator. 390 g (3.59 mol) ethylchloroformate are added dropwise over 1½ hours and the mixture stirred for 4 hours under reflux. A precipitate separated out and is suction filtered. The filtrate is evaporated on a rotary evaporator, the residue is taken up in 400 ml ether, stirred briefly and suction filtered. After washing with ether, the substance is dried in a drying cupboard. (M.p. 151°–152° C.).

4-(4-Fluorobenzyl)-2-(piperazin-4-yl)-1-(2H)-phthalazinone 110.2 g (0.269 mol) of the above-described N-carbethoxypiperidine derivative are added to 181.5 g 48% HBr (1.077 mol) with stirring. Glacial acetic acid is added dropwise to the clear solution and the mixture heated up to a temperature of 100° C. on an oil bath. After 9 hours the solvent is distilled off. To the resulting viscous mass 860 ml water are added with stirring, whereupon a white substance crystallizes out. On addition of 138 ml concentrated ammonia the reaction product precipitates out as a base. The product is suction filtered, washed with water and dried in a drying cupboard at 50° C. (M.p. 157°–159°).

The hydrazino starting material with the radical A wherein R$_5$ represents a methyl group can, for example, also be prepared as follows:

To 120 ml toluene 41.0 g (0.295 mol) tropinone (N-methyl-8-azabicyclo[3.2.1]octane-3-one) and then 22.8 g (0.31 mol) acetylhydrazine are added. The mixture is refluxed for 3 hours and the resulting water is azeotropically distilled off. The resulting product crystallizes out overnight. The remaining solvent is distilled off and the so obtained N-acetyl-N'-[3-(N-methyl-8-azabicyclo[3.2.1]octane]hydrazone recrystallized from 414 ml.—ethyl acetate. (M.p. 155°–157° C.).

58 g (0.297 mol) of this compound, 440 ml glacial acetic acid and 5.8 g PtO$_2$ (81.05%) are then added to a shaking autoclave and a hydrogen pressure of ca. 5.7 bar applied. Hydrogenation is carried out at room temperature. After ca. 4 hours there is no further hydrogen uptake. The catalyst is filtered off and the filtrate concentrated using a rotary evaporator. The N-acetyl-hydrazine compound remains as an oily residue.

The 170.5 g of the oily residue so obtained are added to 1200 ml 22% HCl. The mixture is heated under a nitrogen atmosphere for 8 hours under reflux. The resulting solution is evaporated on a rotary evaporator whereby a crystalline substance remains behind. Removal of any remaining water is effected by adding 150 ml methanol twice and then subsequently evaporating. The residue is dried in a drying cupboard at 50° C. under vacuum. The so obtained 3-hydrazino-N-methyl-8-azabicyclo[3.2.1]octane×2 HCl melts with decomposition at 250° C.

Other starting materials of formula II may be obtained in an analogous manner. The corresponding 2-phenylacetyl-benzoic acids contain the radicals R$_1$ and R$_2$ in the phenylacetyl radical and R$_3$ and R$_4$ in the benzoic acid part. It is therefore convenient first of all to prepare the corresponding compound II whereby R$_5$ of the residue A is a methyl group and to cleave this via the carbethoxy compound. The basic compounds II whereby R$_5$ represents the methyl group may also be produced according to processes analogous to German DOS 21 64 058 and the Vogelsang U.S. patent.

PROCESS (B)

Functional derivatives of the carboxylic acid of the general formula IV which may be used include in particular the acid halides (chloride, bromide, iodide), esters (in particular the $C_1$-$C_6$-alkanolates (as well as) inner esters with an enolized keto group (for example p-chlorobenzylidine phthalides) and the corresponding anhydrides. Compounds of formula IV as well as the corresponding acid halides and esters with $C_1$-$C_6$-alkanolates may also be used in the form of their cyclic tautomers. These cyclic forms may be represented by the following formula:

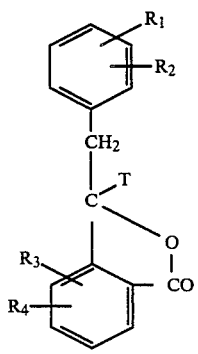

In this formula, T represents a hydroxy group, halogen or $C_1$-$C_6$-alkoxy.

The reaction may be carried out in the presence or absence of conventional solvents and auxiliary agents at temperatures between 40° and 200° C. and over a wide pH range from acid up to alkaline.

Suitable solvents which may be used include, for example, water, aromatic hydrocarbons such as, for example, benzene, mesitylene, toluene, xylene; halogenated hydrocarbons such as, for example, chloroform, 1,2-dichloroethane, tetrachloromethane, chlorobenzene, methylene chloride; ethers such as, for example, tetrahydrofuran, dioxane, diisopropyl ether; sulphoxides such as, for example, dimethylsulphoxide, tertiary acid amides such as, for example, dimethylformamide, dimethylacetamide, hexamethylphosphoric acid amide, tetramethyl urea, N-methylpyrrolidone; lower alcohols, such as, for example, methanol, ethanol, isopropanol, amyl alcohol, butanol, tertiary butanol and mixtures of the above agents as well as tertiary amines such as, for example, pyridine. Auxiliary agents which may be used include bases, acids and conventional condensation agents for these reactions.

The compounds of formula V may also be employed in the form of their N-acyl derivatives whereby these are first hydrolyzed and then without further purification or isolation immediately further employed in the same reaction medium with the compound of formula IV.

For the conversion of such benzylphthalazinone derivatives which are obtained when Z represents hydrogen in the formula V with a compound of the formula Y-A, the above identified solvents may also be used as well as the above identified temperature range.

Other solvents which may also, especially, be used include tertiary acid amides (for example dimethylformamide), aromatic hydrocarbons (for example toluene, lower alcohols or water, whereby the reaction is often carried out in the presence of basic substances (for instance alkali hydroxides or alkali alcoholates). The temperature used is preferably from 50°-200° C., and more preferably from 80°-150° C. If Y represents a halogen atom in formula VI, then this may be chlorine, bromine or iodine. If Y in formula VI is a sulphonic acid ester group, this may, for example, be a $C_1$-$C_6$-alkylsulphonic acid radical (for example $CH_3$—$SO_2$—O—) or an arylsulphonic acid radical such as, for example, a $C_1$-$C_4$-alkylbenzene sulphonic acid (for example the p-toluene sulphonic acid radical). The benzyl-phthalazinone starting material (compound of formula I whereby in place of the radical A on the acid amide nitrogen atom a hydrogen atom is present) may, for example, also be employed in the form of their alkali (Na, K) salts. Such alkali salts may, for example, be obtained from the corresponding phthalazinone and the alkali metal in an alcoholic solution (for example ethanol) or using another conventional agent therefor between 40°-100° C. Where the radical Z represents hydrogen in the starting material of formula V, a compound of formula VI is obtained from the subsequent reaction with the resulting 4-benzylphthalazinone whereby A is either the A is either the radical

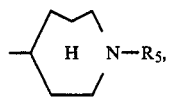

or the radical

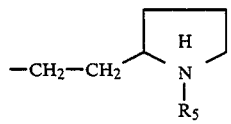

as end product each time mixtures of compounds of the formula I wherein A is the hexahydroazapine radical

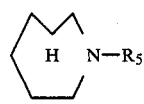

and compounds of formula I wherein A represents the 2-pyrrolidine ethyl radical

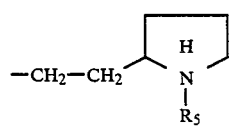

(cycloammonium rearrangement). The isolation of the corresponding pure compound may, for example, be carried out in a conventional manner by fractional crystallization.

Preparation of starting materials of formula V

Such starting materials may, for example, be prepared as follows:

Conversion of the corresponding cyclic ketones of the formula O=A' with acetyl hydrazine (for example in an aromatic hydrocarbon (toluene) between 50°-150° C.) or benzoyl hydrazine (for example in an aliphatic alcohol between 20°-100° C.) to the corresponding hydrazones, followed by subsequent reduction of the same by catalytic hydrogenation (for example in glacial acetic acid in the presence of $PtO_2$ at a pressure of 5–6 bar) or reduction using a complex metal hydride ($NaBH_4$) in an inert reagent (lower alcohols such as methanol or dioxane) followed by subsequent hydrolytic cleaving off of the acyl group using dilute hydrochloric acid (20–37%). In the case of ketones of the formula O═A′, A′ represents the radical A, whereby via the tertiary carbon atom (by means of which A is bonded to the phthalazinone radical) in place of a hydrogen bond, there is a second bond with the keto oxygen. A further possibility is, for example, the reaction of the acylhydrazine (for example benzene hydrazine) with a compound of the formula VI in an inert agent (for example dimethylformamide) between 50° and 180° C. in the presence of an acid-binding agent (a tertiary amine).

The various $R_5$ radicals may, for example, be obtained before the reaction with the acylhydrazine from the cyclic ketones in which $R_5$ represents hydrogen by reaction with a compound of the formula $R_5X$ (X═Cl, Br, I or an alkyl or arylsulphonic acid radical) in an inert solvent, for example in the presence of a basic compound at a temperature between 20° and 200° C.

Starting materials of the formula IV may, for example, be prepared in known manner using the conventional Perkin synthesis from a phthalic acid anhydride containing the radicals $R_3$ and $R_4$ and the radicals $R_1$ and $R_2$ substituted by phenylacetic acid.

The introduction of a $C_2$-$C_6$-alkanoyl group by acylation is effected by the corresponding acylation of compounds of formula I wherein the radicals $R_1$, $R_2$, $R_3$ and/or $R_4$ represent hydroxy groups, amino groups or $C_1$-$C_6$-alkylamino groups. The acylation is carried out by means of a $C_2$-$C_6$-alkane carboxylic acid whereby this is preferably activated. If such an activated acid is used for the acylation, this will preferably be a compound of the formula $C_2$-$C_6$-alkanoyl-W, wherein W represents halogen (for example chlorine or bromine), but may, for example, also be a group of the formula —OR′, —SR′ or a group of the formula —$OSO_3H$ or —OCO—R″ and R′ represents a $C_1$-$C_6$-alkyl radical or also a phenyl radical, which may be substituted by nitro groups, $C_1$-$C_4$-alkoxy groups, $C_1$-$C_4$-alkyl groups or halogen atoms (chlorine, fluorine, bromine), a cyanomethyl radical or a carboxymethyl radical and R″ represents a straight or branched chain $C_1$-$C_5$-alkyl radical. Where W represents a halogen atom, this is preferably a chlorine, bromine or iodine atom; in the case where R′ or R″ represent alkyl, alkylthio or alkoxy radicals, these are preferably of low molecular weight and contain from 1–4 carbon atoms. Frequently and in particular when W represents a halogen atom or the group —O—COR″, the presence of an acid-binding agent such as an alkali metal hydroxide an alkali metal carbonate, an alkali metal bicarbonate, an alkali metal acetate, an alkaline earth carbonate, a tertiary amine (trialkylamines such as triethylamine, pyridine) or also alkalihydrides and the like is desirable. The acid-binding agent may also be used alone or in admixture with other conventional agents as solvents (for example pyridine). If the free acid is used, then this may be activated by the presence of condensing agents such as, for example, dicyclohexylcarbodiimide, tetraethyl pyrophosphite, 5-(3′-thiophenyl)-ethylisooxazole, sulphurous acid-bis-alkylamides (for example $SO[N(CH_3)_2]_2$, N,N′-carbonyldiimidazole and the like (Organic Reactions, Vol. 12, 1962, pages 205 and 239).

Introduction of a $C_1$-$C_6$-alkyl group or of the benzyl group is effected by alkylation (or benzylation) of compounds of formula I in which the radicals $R_1$, $R_2$, $R_3$ and/or $R_4$ represent hydroxy groups, amino groups or alkanoylamino groups.

This alkylation (or benzylation) may, for example, be effected by treatment of compounds of the formula $C_1$-$C_6$-alkyl-hal, benzyl-hal, $ArSO_2O$-$C_1$-$C_6$-alkyl and $SO_2(O$-$C_1$-$C_6$-alkyl)$_2$, whereby hal may represent a halogen atom (preferably chlorine, bromine or iodine) and Ar represents an aromatic radical (for example a phenyl or naphthyl radical which may, for example, be substituted by one or more lower alkyl radicals). Examples of such groups are p-toluene sulphonic acid-$C_1C_6$-alkyl esters, $C_1$-$C_6$-dialkyl sulphates, $C_1$-$C_6$-alkyl halogenides and the like. The alkylation reaction is preferably carried out in the presence of conventional acid-binding agents. Acid-binding agents which may, for example, be used include those already mentioned for the acylation.

The acylation or the alkylation may, for example, be carried out at temperatures between −20° and 220° C., preferably 0°–150° C., in particular 20° and 80° C. in inert solvents or suspension agents. Solvents or dispersing agents which may, for example, be used include: aromatic hydrocarbons such as, for example, benzene, toluene, xylene; aliphatic ketones such as, for example, acetone, methylethyl ketone; halogenated hydrocarbons such as, for example, chloroform, tetrachloromethane, chlorobenzene, methylene chloride; aliphatic ethers such, as for example, butyl ether; cyclic ethers such as, for example, tetrahydrofuran, dioxane; sulphoxides such as, for example, dimethylsulphoxide; tertiary acid amides, such as, for example, dimethylformamide, N-methylpyrrolidone, hexamethyl phorphoric acid amide; aliphatic alcohols such as methanol, ethanol, isopropanol, amyl alcohol, tertiary butanol, cycloaliphatic hydrocarbons, such as cyclohexane and the like. Aqueous mixtures of the above-mentioned solvents may also be used. The reaction is often carried out at the reflux temperature of the solvents or dispersing agents used. The alkylation reaction component is often used in excess. The alkylation may also be carried out in the presence of tetraalkyl ammonium salts (in particular the halides) in combination with alkali hydroxides at temperatures between 0°–100° C., preferably 20°–80° C. in an aprotic solvent or also in chloroform or methylene chloride. Aprotic solvents which may be used include in particular: tertiary amides (dimethylformamide, N-methylpyrrolidone, hexamethyl phosphoric acid triamide), dimethylsulphoxide, acetonitrile, dimethoxyethane, acetone, tetrahydrofuran. With the acylation and alkylation it is also possible to proceed in a manner such that an alkali compound of the compound to be treated is first prepared in that it is added to an inert solvent such as dioxane, dimethyl formamide, benzene or toluene with an alkali metal, alkali hydride or alkali amide (in particular sodium or sodium compounds) or butyl lithium at temperatures between 0° and 150° C. and the compound to be acylated or alkylated is then added.

In place of the above-mentioned alkylating or acylating agents other chemically equivalent agents commonly used in chemistry may be used. (See, for example, also L. F. and Mary Fieser "Reagents for Organic Synthesis", John Wiley and Sons. Inc., New York, 1967, Vol. 1. pages 1303–4 and Vol. 2, page 471).

The acyl groups in compounds of formula I may be split off using solvolysis whereby the corresponding compounds of formula I are obtained containing free hydroxy groups, amino groups or $C_1$-$C_6$-alkylamino groups. This solvolytic cleaving reaction may, for example, be carried out by saponification using dilute acids or using basic materials (potash, soda, aqueous alkali solutions, $NH_3$) at temperatures between 10° and 150° C., in particular 20°–100° C.

Depending on the reaction conditions and the starting materials, the end products of formula I may be obtained in free form or in the form of one of their salts. The salts of the end products may be converted to their bases in a conventional manner, for example, with alkali or ion exchange agents. From the latter, salts may be prepared by treatment with organic or inorganic acids, in particular those which are suitable for the preparation of therapeutically acceptable salts.

The compounds of formula I according to the present invention contain in some cases an asymmetric carbon atom (for example the C atom of the 7-ring which is bound to the acid amide nitrogen of the phthalazinone) and are usually obtained in the form of their racemates. Such racemates may be resolved in a conventional manner, for example by fractional crystallization of the salts of racemic compounds of formula I with optically active acids or also by chromatographic racemate separation (see, for example Angewandte Chemie 92/1 (1980) page 14) into their optically active isomers. It is, however, also possible to use an optically active starting material, whereby the end product is then obtained in the corresponding optically active form. In the case of further asymmetric C-atoms, one obtains diastereomeric mixtures. Separation can be achieved using conventional methods.

The present invention thus also covers racemates and diastereomeric forms as well as the corresponding optically active right and left rotating forms.

The compounds of the present invention are suitable for the preparation of pharmaceutical compositions and formulations. The pharmaceutical compositions or medicaments may contain as active ingredient one or more compounds of the present invention which may be in admixture with other pharmacologically or pharmaceutically active substances. The preparation of medicaments can be carried out using known and conventional pharmaceutical carriers and auxiliary agents.

The compositions can comprise, consist essentially of or consist of the stated materials and the processes can comprise consist essentially of or consist of the recited states with such materials.

EXAMPLE 1

4-(p-Chlorobenzyl)-2-[hexahydro-1-(p-methylbenzyl)azepin-4-1]-1-(2H)-phthalazinone 0.016 mol (7 g) 4-(p-Chlorobenzyl)-2-(hexahydroazepin-4-yl)-1-(2H)-phthalazinone hydrobromide are dissolved in 50 ml dioxane at 50° C. 0.048 mol (6.5 ml or 4.7 g) triethylamine are added to this solution with stirring as well as 0.016 mol (2.1 ml or 2.2 g) 4-methylbenzyl chloride. The mixture is then stirred for 5 hours at 85° C. The mixture is allowed to cool to room temperature, filtered and concentrated on a rotary evaporator. The dark oily residue is dissolved in propanolic hydrochloric acid and a viscous oily product is then precipitated by the addition of ether. The upper layer of solvent is decanted off. The oily residue is covered with ether and allowed to stand overnight in a closed flask at room temperature. The somewhat hard substance is then trituated in portions with ether, the solvent filtered off and the product dried in the air.

The product is then dissolved in warm methylethylketone, ether is added until cloudiness occurs and the salt is then allowed to crystallize out overnight. The filtered product is dried in vacuo.

Yield: 3.4 g (43%).
M.p. 191°–195° C. (Hydrochloride).

The starting material may, for example, be prepared as follows:

60 g (0.157 mol) 4-(p-chlorobenzyl)-2-(hexahydro-1-methyl azepin-4-yl)-1-(2H)-phthalazinone are dissolved by warming to 95° C. in 600 ml dry toluene. 51.1 g (0.471 mol=45 ml) ethyl chloroformate in 45 ml toluene are then added dropwise With stirring. The mixture is stirred for 5 hours at 95° C. After cooling to room temperature the reaction mixture is suction filtered from the insoluble material and dried on a rotary evaporator. An oily residue is obtained which is triturated with a little ether and crystallizes as a white product, which melts at 103°–105° C. (yield: 53.4 g (77%).

53.4 g (0.12 mol) of the so obtained 1-carbethoxy derivative (formula I, $R_5$ in radical A=$COOC_2H_5$) and 114 ml of a 40% solution of hydrobromic acid in glacial acetic acid are heated to 85°–90° C. under vigorous stirring for 4 hours; with increasing heating the carbethoxy compound dissolves. After cooling the solution is concentrated under vacuo. From the so obtained viscous oily residue the starting material of formula I wherein $R_5$ represents hydrogen is obtained by recrystallization from methanol in the form of a white crystalline hydrobromide.

The solvent is suction filtered, the mixture washed several times with methanol and dried in vacuo.

Yield: 51 g (95%)
M.p. 138°–140° C.

For the preparation of the free base the hydrobromide is suspended in 300 ml distilled water and made alkaline with 100 ml concentrated ammonia. After 2 hours' stirring the mixture is suction filtered and washed with water until the remain neutral. The white product is dried for several days in a vacuum dessicator over $P_2O_5$.

Yield: 125 g (77% of theory)
M.p.: 123°–125° C.

In a manner analogous to that set out in Example 1 compounds of formula I are obtained which are set out in table 1. Unless otherwise indicated, the melting point given in column 4 is that of the corresponding hydrochloride. For Examples 2 to 8 the molecular amounts of the starting materials II and III are in each case the same. In the case of Examples 9, 10, 11 and 13 in each case 0.027 mol and in the case of Example 12, 0.015 mol of the starting material of formula II are employed. In the case of Examples 5 to 11 as well as 13 the starting material is employed in the form of the free base and in Examples 1 to 4 and 12 in the form of the hydrobromide.

The working up of the reaction product after concentration or removal of the reaction solution is carried out in Examples 6, 7, 10 and 13 in a manner analogous to that given in Example 1.

In the case of Examples 2 and 8 after concentration of the 20 reaction mixture the so obtained residue (following crystallization) is recrystallized prior to salt formation with isopropanolic acid HCl from isopropanol, in the case of Example 3 from methanol, and of Example 5 from ethanol.

In Examples 4, 9, 11 and 12 the residue of the reaction mixture after concentration (optionally after stirring with isopropanol and ether) is first purified using kieselgel and then, after removal of the elution agent with isopropanolic hydrochloric acid to give the hydrochloride. The eluting agent is dichloromethane/methanol/ammonia 25%=85/15/1.

In Example 12, after chromatographic purification the base as dissolved in acetone and the oxalate obtained by the addition of anhydrous oxalic acid dissolved in acetone. In the case of Example 9, the residue from the chromatographic step is not converted into a salt.

In order to obtain the crystalline salts it is where appropriate generally necessary to effect repeated trituration with ethanol or methylethyl ketone; sometimes it is recommended to liberate the base with concentrated ammonia, to shake with ether, dry and reform the salt with isopropanolic hydrochloric acid in isopropanol or methylethyl ketone and to precipitate the salt by the addition of ether (Example 13). The so obtained salt may be recrystallized once more from a suitable solvent (for example isopropanol).

The starting material II for Examples 2 to 4 as well as 9 to 13 is in each case 4-(p-chlorobenzyl)-2-(hexahydro-azepin4-yl)-1-(2H)-phthalazinone. The starting material II (4-(p-fluorobenzyl)-2-(hexahydro-azepine-4-yl)-1-(2H)-phthalazinone) for Examples 5 to 8 may, for example, be obtained as follows:

50 g (0.136 mol) well dried 4-(fluorobenzyl)-2-(hexahydro-1-methylazepin-4-yl)-1-(2H)-phthalazinone are dissolved in 400 ml toluene by warming to 80° C. Should drops of water form on the inner wall of the flask, then this residual water is distilled off by means of an azeotropic water separator.

Subsequently 44.5 g (0.408 mol=38 ml) ethyl chloroformate are added dropwise and stirred for 1-½ hours. After cooling to room temperature the undissolved components are suction filtered off and the so obtained solution dried in vacuo. The remaining syrup which crystallizes out on its own is triturated with ether. The so obtained white crystalline product is suction filtered, washed with ether and dried.

Yield: 33 g (57%)

M.p. 95°-96° C.

A mixture of 33 g (0.078 mol) of the so obtained compound and 65 ml of 40% HBr/glacial acetic acid is slowly heated to 100° C. on an oil bath and stirred for 2 hours. The reaction product is allowed to cool and reduced on a rotary evaporator. The oily residue is dissolved in 250 ml distilled water and the solution made alkaline by the addition of 40 ml concentrated ammonia. The base then precipitates out as a crystalline substance, is suction filtered and dried in a dessicator over phosphorous pentoxide.

Yield: 23 g (48%)

M.p.: 86°-88° C.

The 4-(fluorobenzyl)-2-(hexahydro-1-methylazepin-4-yl-1-(2H)-phthalazinone for example was obtained as follows 230 g (0.809 mol) of N-benzoyl-N'-(1-methyl-hexahydroazepin-4-yl)-hydrazine was heated for 4 hours with 830 ml of 23% hydrochloric acid under reflux (benzoic acid precipitated out. Cooling was carried out and concentration on a rotary evaporator, about 200 ml of toluene added and concentration carried out again. The residue was boiled for 2.5 hours with 209 g of 2-(4-fluorophenacetyl)-benzoic acid, 149.5 g of 85% KOH and 2300 ml of methanol. The mixture was concentrated and the residue stirred with 3.3 liters of H₂O and 785 ml of 2 molar NaOH. The base precipitated out. The product was stirred further filtered with suction and washed neutral with H₂O. The product was dried at 50° C. in a vacuum.

TABLE 1

| Example No. | $R_1$ $R_2 = H$ | A = 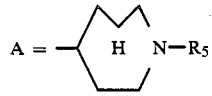 $R_5$ | M.p. (hydrochloride) °C. | Yield in % | Starting material Cl—$R_3$ in mol | Triethylamine in mol | Temp. of reaction/ duration (hrs.) |
|---|---|---|---|---|---|---|---|
| 2 | p-Cl | 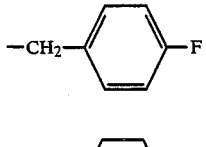 | 145 | 68 | 0.016 | 0.048 | 90° C./5 |
| 3 | p-Cl | 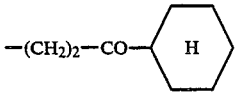 | 204–7 | 30 | 0.013 | 0.032 | 95° C./4 |
| 4 | p-Cl | 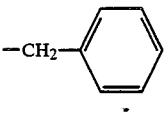 | 140 | 25 | 0.0156 | 0.47 | 85° C./5 |
| 5 | p-F |  | 197–199 | 65 | 0.02 | 0.04 | 85–90° C./3 |
| 6 | p-F | —CH₂—CH=CH₂ | 180–182 | 64 | 0.02 | 0.04 | 75° C/3 |

TABLE 1-continued

| Example No. | R₁ R₂ = H | A = $-\left\langle\begin{array}{c}\overset{\curvearrowleft}{H}\;N-R_5\end{array}\right\rangle$  R₅ | M.p. (hydrochloride) °C. | Yield in % | Starting material Cl—R₃ in mol | Triethylamine in mol | Temp. of reaction/ duration (hrs.) |
|---|---|---|---|---|---|---|---|
| 7 | p-F | —CH₂—CH₂—C₆H₅ | 212–215 | 40 | 0.014 | 0.028 | 95° C./4 |
| 8 | p-F | —CH₂—C₆H₄—F | 197–200 | 45 | 0.014 | 0.028 | 80° C./3 |
| 9 | p-Cl | —CO—CH=CH—C₆H₅ | 204–206 Base | 55 | 0.054 | 0.081 | 20–23° C./8 |
| 10 | p-Cl | —CH₂—CH=CH—C₆H₅ | 224–226 Decomposition | 69 | 0.054 | 0.081 | 101° C./13 |
| 11 | p-Cl | —CH₂—cyclopropyl | 226–228 Decomposition | 53 | 0.054 | 0.081 | 101° C./13 |
| 12 | p-Cl | —(CH₂)₂—O—(CH₂)₂—OH | 112–116 Oxalate | 49 | 0.018 | 0.027 | 101° C./8 |
| 13 | p-Cl | —(CH₂)₂—N(CH₃)₂ | 248–250 (2HCl) | 44 | 0.054 | 0.054 | 101° C./4 |

EXAMPLES 14 TO 43 (Tables 2 and 3)

The preparation of compounds of formula I according to Examples 14 to 38 is carried out according to the following procedure:

10 mol dioxane, 3 mol triethylamine and 2 mol of the starting material of formula III are added to 1 mol of the starting material of formula II (free base) at room temperature. The reaction mixture is then heated for several hours at 100° C. and after concentration the resulting material is poured into distilled water. The product is worked up according to Method A or B.

METHOD A

The oil, which is insoluble in water, is extracted twice with ether, the combined ethereal extracts are shaken once with water and dried over Na₂SO₄. After evaporation the remaining oil is taken up in a mixture of isobutylmethyl ketone (or ethylmethylketone) and toluene, acidified using isopropanolic hydrochloric acid and, if necessary, concentrated slightly. After seeding the warm solution with crystals obtained in a reagent glass (and/or addition of ether) a crystalline product is obtained.

Method B

The oil, which is insoluble in water, is extracted three times with methylene chloride and the combined organic phases are shaken twice with water. The resulting organic phase is dried over Na₂SO₄ and concentrated using a rotary evaporator, the residue is taken up in 50–70 ml acetone and triturated with 20 g kieselgel (which serves to absorb the starting material). After stirring for 10 minutes the kieselgel is removed by suction filtration and the filtrate concentrated. The residue after evaporation is taken up in methyl ketone/toluene, acidified with isopropanolic HCl and the solution is concentrated until cloudiness persists. Crystallization may, if necessary, be encouraged by the addition of ether. The resulting crude product is suction filtered, washed with acetone and refluxed with CH₂Cl₂/methyl ketone. After being allowed to stand for several hours, the pure product is obtained by suction filtration, washed with a large amount of acetone and diethyl ether and the resulting crystals are dried under a vacuum at 50° C.

In the case of Examples 14 to 24, a starting material of Formula II is employed wherein R₁ represents a chlorine atom in the p-position, for Examples 25–43 a starting material of Formula II is employed wherein R₁ represents a fluorine atom in the p-position. In Table 2, A always represents the radical

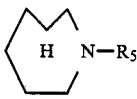

in Table 3, A always represents the radical

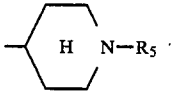

The starting materials of Formula III for Examples 14 to 43 are chlorides of the formula Cl-R₅, wherein R₅ has the meanings given in column 2 of Table 2 or Table 3.

The letter D alongside the melting point temperature means that the relevant substance melts with decomposition.

The products of the process according to the Examples 16, 19, 22, 24, 31 and 33 of Table 2 as well as Example 37 of Table 3 each contain one-molecule of water of crystallization.

The preparation of compounds of Formula I according to Examples 39-43 is carried out (see Table 3) according to the following working procedure (the reaction temperature and the solvents are here set out in the last column of Table 3):

0.05 mol of the starting material of Formula II (free base) are added to the solvent and dissolved with stirring at a temperature of from 40°-50° C. This is followed by the addition of the proton-accepting agent ($K_2CO_3$ or triethylamine) and the dropwise addition of starting material III (Cl-$R_5$). The reaction mixture is refluxed for several hours or stirred at a given temperature. After cooling to room temperature the precipitated salts are suction filtered and the filtrate is concentrated on a rotary evaporator. The residue is worked up and the resulting product is purified by recrystallization or column chromatography. In most cases there is a subsequent salt formation in order to improve solubility. In order to obtain the hydrochloride the base is suspended in ethylmethyl ketone or isopropanol, isopropanolic hydrochloric acid is added until an acidic reaction is obtained and stirred with diethyl ether until the first slight cloudiness appears. The corresponding oxalate is obtained by dissolving the substance in acetone and adding anhydrous oxalic acid which is also dissolved in acetone.

In Examples 39, 40, 41 and 43 dioxane is used at the solvent and triethylamine as the basic compound (in the case of Example 43 0.15 mol triethylamine, in other cases 0.1 mol). In the case of Example 42 dimethylacetamide is used as the solvent and 0.1 mol $K_2CO_3$ is used as the basic compound. The amount of starting material of Formula III $R_5$-Cl is 0.06 mol in Examples 39-41 and 0.1 mol in both Examples 42 and 43.

Working up: In Examples 39-41 the residue after distillation of the reaction mixture is recrystallized from ethanol (50-250 ml) with the addition of active charcoal (in the case of Example 41 kieselgel addition) and subsequently the hydrochloride is formed. In the case of Examples 42 and 43 the oily residue is stirred in each case with 50 ml diethylether which results in crystallization. In the case of Example 43 a subsequent chromatography through a kieselgel column (eluent: dichloromethane/methanol/ammonia 25%=85/15/1).

In Examples 14-43 $R_2$ is always hydrogen.

TABLE 2

A = 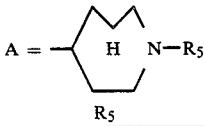

| Example No. | $R_5$ | M.p. °C. (hydrochloride) | Yield in % | Reaction time (hrs) | Working up method |
|---|---|---|---|---|---|
| 14 | 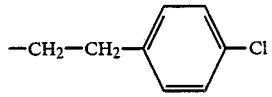 | 218-223 | 20 | 10 | B |
| 15 | 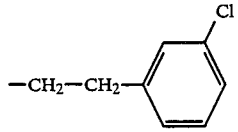 | 210-214 | 34 | 8 | A |
| 16 | 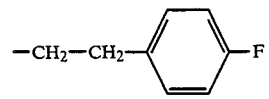 | 180-186 | 37 | 12 | B |
| 17 | 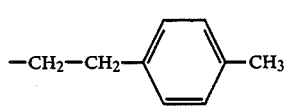 | 225-231 | 49 | 12 | B |
| 18 | 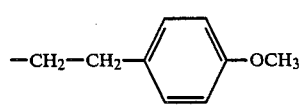 | 205-208 | 36 | 16 | B |
| 19 | 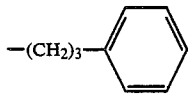 | 192-195 | 77 | 5 | B |
| 20 | 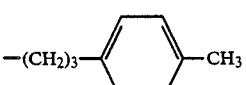 | 207-212 D | 80 | 1 | A |

TABLE 2-continued

| Example No. | A = cyclohexyl-H, N-R5; R5 | M.p. °C. (hydrochloride) | Yield in % | Reaction time (hrs) | Working up method |
|---|---|---|---|---|---|
| 21 | —(CH₂)₃—C₆H₄—OCH₃ | 228–234 D | 33 | 5 | A |
| 22 | —(CH₂)₃—C₆H₄—F | 204–207 | 90 | 2 | B |
| 23 | —(CH₂)₃—C₆H₄(o-F) | 189–194 | 33 | 6 | A |
| 24 | —(CH₂)₃—C₆H₃(OCH₃)₂ | 123–135 D | 20 | 6 | B |
| 25 | —CH₂—CH₂—C₆H₄—F | 194–197 | 30 | 10 | B |
| 26 | —CH₂—CH₂—C₆H₄—Cl | 215–219 D | 33 | 10 | A |
| 27 | —CH₂—CH₂—C₆H₄(m-Cl) | 215–218 D | 34 | 3 | A |
| 28 | —CH₂—CH₂—C₆H₄—CH₃ | 241–244 D | 30 | 8 | A |
| 29 | —CH₂—CH₂—C₆H₄—OCH₃ | 182–186 D | 23 | 10 | A |
| 30 | —CH₂—CH₂—C₆H₂(OCH₃)₃ | 181–186 D | 46 | 16 | B |
| 31 | —(CH₂)₃—C₆H₄—OCH₃ | 185–191 D | 50 | 4 | B |

TABLE 2-continued

| | A = [pyrrolidine with H, N—R₅] | | | | |
|---|---|---|---|---|---|
| Example No. | R₅ | M.p. °C. (hydrochloride) | Yield in % | Reaction time (hrs) | Working up method |
| 32 | —(CH₂)₃—C₆H₄—F (para) | 207–211 | 29 | 4 | B |
| 33 | —(CH₂)₃—C₆H₄—F (meta) | 190–193 | 15 | 4 | B |
| 34 | —(CH₂)₃—C₆H₄—F (ortho) | 189–191 | 69 | 6 | B |

TABLE 3

| | A = [piperidine with H, N—R₅] | | | | Volume of solvent/ |
|---|---|---|---|---|---|
| Example No. | R₅ | M.p. °C. (hydrochloride) | Yield in % | Reaction time (hrs) | Working up method | Reaction temperature (see p. 41) |
| 35 | —(CH₂)₃—C₆H₅ | 209–211 | 90 | 5 | A | |
| 36 | —(CH₂)₃—C₆H₄—F | 191–195 | 62 | 2 | B | |
| 37 | —(CH₂)₃—C₆H₂(OCH₃)₃ | 172–176 | 64 | 13 | B | |
| 38 | —(CH₂)₂—C₆H₄—OCH₃ | 191–195D | 63 | | B | |
| 39 | —CH₂—C₆H₅ | 219–221 | 53 | 3 | | 120/85–90° C. |
| 40 | —CH₂—CH=CH₂ | 157–158 | 57 | 3 | | 120/70° C. |
| 41 | —(CH₂)₂—C₆H₅ | 246–248 | 59 | 8 | | 120/101° C. |
| 42 | —(CH₂)₂—OCH₃ | 180–183 | 46 | 6 | | 115/120° C. |

TABLE 3-continued

| Example No. | $A = -\langle H \quad N-R_5 \rangle$ $R_5$ | M.p. °C. (hydro-chloride) | Yield in % | Reaction time (hrs) | Working up method | Volume of solvent/ Reaction temperature (see p. 41) |
|---|---|---|---|---|---|---|
| 43 | $-CH_2-CH\begin{matrix}CH_2\\ \\CH_2\end{matrix}$ | 195–197 | 15 | 16 | | 70/101° C. |

EXAMPLES 44–48

The preparation of compounds of Formula I ($R_1$=fluorine in the 4-position; $R_2$=hydrogen; A see Table 4) according to Examples 44–48 is carried out according to the following working procedure:

0.011 mol of the starting material of Formula II (free base) are taken up in 50 ml dioxane (30 ml dioxane in the case of Example 48; 25 ml dioxane in the case of Example 49) and dissolved with stirring at a temperature of 40°–50° C. 0.033 mol triethylamine (in the case of Example 49 0.013 mol) are added in each case followed by the dropwise addition of the starting material of Formula III (Cl-$R_2$). The reaction mixture is refluxed for several hours or stirred at a given temperature. After cooling to room temperature the precipitated salts are dried on a suction filter and the filtrate concentrated on a rotary evaporator. The residue is worked up and the resulting product purified by recrystallization (Examples 44, 45, 47 and 48) or column chromatography (Example 46). Elution agent: dichloromethane/methanol/ammonia 25%=85/15/1. In most cases salt formation is effected to improve solubility. In order to obtain the hydrochloride the base is suspended in ethylmethyl ketone or isopropanol, treated with an isopropanolic HCl until an acidic reaction is obtained and diethylether is added until the first slight cloudiness occurs.

TABLE 4

| Example No. | $A = -\langle H \quad N-R_5 \rangle$ $R_5$ | M.p. (hydro-chloride) °C. | Yield in % | Starting material III Cl—$R_2$ in Mol | Temp. of reaction/ duration (hrs.) |
|---|---|---|---|---|---|
| 44 | $CH_2-CH=CH_2$ | 135–140 sinters at 130° C. | 73 | 0.033 | 101° C./8 |
| 45 | $CH_2-\langle H \rangle$ | 156–157 (Base) | 45 | 0.047 | 101° C./24 |
| 46 | $CH_2-CH\begin{matrix}CH_2\\ \\CH_2\end{matrix}$ | 152–160 | 26 | 0.054 | 101° C./32 |
| 47 | $-(CH_2)-CO-\langle H \rangle$ | 143–146 | 56 | 0.033 | 101° C./6 |
| 48 | $-(CH_2)_2-\langle\bigcirc\rangle$ | 245–247 | 30 | 0.033 | 101° C./10 |
| 49* | $-CH_2-\langle\bigcirc\rangle$ $R_1$ = p-Cl | 230–232 | 53 | 0.0065 | 90° C./6 |

EXAMPLES FOR PROCESS (B)

EXAMPLE 50

4-(4-Fluoro-benzyl)-2-(hexahydro-1-benzylazepin-4-yl)-1-(2H)-phthalazinone

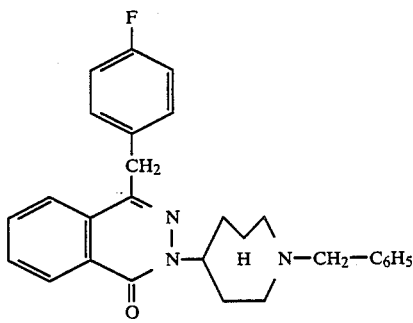

34 g (0.088 mol) 1-benzoyl-2-(hexahydro-1-benzylazepin-4-yl)-hydrazine×HCl are refluxed together with 90 ml 23% HCl for 4 hours under stirring. After cooling the reaction mixture is rotated in a vacuum to effect drying. The remaining residue is admixed with 22.7 g (0.088 mol) of 2-(p-fluorophenacetyl)-benzoic added and 14 g (0.25 mol) potassium hydroxide dissolved in 250 ml methanol and the solution subsequently stirred for 2 hours at room temperature. Finally the solvent is distilled off in vacuo and the residue is treated with 500 ml H₂O and 85 ml 2N NaOH. The reaction product precipitates out with stirring in the form of its base as a crystalline precipitate which is filtered off and thoroughly washed with H₂O. The product is dried in a dessicator over phosphorous pentoxide and recrystallized from isopropanol.

Yield: 26 g
M.p. 197°–199° C.

The starting materials may, for example, be obtained as follows:

1-Benzoyl-2-(hexahydro-1-benzylazepin-4-yl)-hydrazine×HCl

A mixture of 68.3 g (0.27 mol) N-benzylazepine-one-(4)-hydrochloride, 38 g (0.28 mol) benzoylhydrazine and 250 ml methanol are stirred for 1.5 hours at 30° C. until solution takes place. After cooling to 4° C., 15.3 g (0.27 mol) potassium hydroxide dissolved in 150 ml methanol are added dropwise with stirring whilst maintaining the above temperature (ice cooling). After addition has taken place 15.8 g (0.42 mol) sodium borohydride are added in small portions over a period of 1 hour with maintenance of the temperature of the reaction medium at 14°–18° C. (exothermic reaction; strong foaming due to H₂ production) and the reaction mixture is subsequently stirred at room temperature 20 for a further 2 hours. Subsequently 120 ml isopropanolic hydrochloric acid are added to bring the pH of the reaction mixture to 5 and stirring is carried out for 2 hours under ice water cooling. After filtering off the inorganic salts, the filtrate is concentrated in vacuo. The remaining oil is treated with 250 ml acid/methanol=10:1. The hydrochloride precipitates out as a crystalline product on stirring. The precipitate is suction filtered and dried.

Yield: 27 g (35%)
M.p. 176°–180° C.

2-(p-Fluoro-phenacetyl)-benzoic acid 250 g (1.04 mol) p-Fluoro-benzylidene phthalide are added to 410 ml (3.9 mol) 29% sodium hydroxide using an oil bath temperature of 70° C. with stirring. Towards the end of the addition the oil bath temperature is raised to 110° C. A red colored oil is thereby obtained. On cooling, this oil precipitates as a crystalline product. This substance is dissolved in 500 ml distilled water (red-colored solution) and the solution is acidified under stirring by dropwise addition of 340 ml concentrated hydrochloric acid. The precipitate is suction filtered, washed several times with distilled water and dried in a vacuum. Finally, the product is recrystallized from toluene.

Yield 220.8 g (82%)
M.p. 146°–150° C.

In an analogous manner to the above example compounds of Formula I may be obtained (for example the compounds given in Tables 1 to 4) from in each case 0.088 mol of phenacetylbenzoic acid substituted by the radicals $R_1$, $R_2$, $R_3$ and $R_4$ (for example 2-(p-chlorophenacetyl)-benzoic acid or 2-(p-fluorophenacetyl)-benzoic acid) and 0.088 mol of a hydrazine of the formula

The hydrazine may in this case be employed in the form of its acyl derivative (benzoyl or acetyl derivative) in which case, before the actual reaction the acyl group is split off giving the free hydrazine.

The hydrochlorides may, for example, be obtained by treatment of the corresponding base with isopropanol/HCl, followed by precipitation with ether and recrystallization from ethyl methyl ketone ether.

4-(3,4-Dichlorobenzyl)-2-(hexahydro-1-benzyl-azepin-4-yl)-1(2H)-phthalazinone

EXAMPLE 51

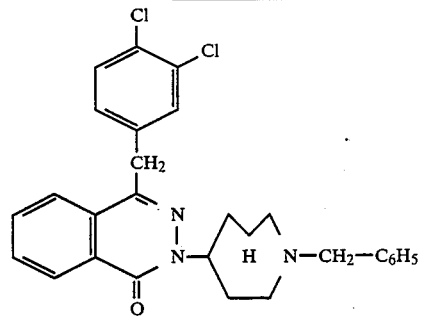

A solution of 3.28 grams (8.15 mmoles) of 4-(3,4-dichlorobenzyl)-2-(hexahydro-1H-azepin-4-yl)-1-(2H)-phthalazinone, 3.4 ml (29.5 mmol) of benzyl chloride and 9 ml (64.6 mmol) of triethylamine in 20 ml of dioxane were heated for 12 hours at 200° C.

Then the mixture was concentrated, the residue treated with water and shaken with dichloromethane. The organic phase was dried with MgSO₄, filtered and concentrated. The oil remaining behind crystallized overnight. The crystals were suspended in ether and stirred. After filtering with suction and washing the material with ether the solution was rotated.

There resulted a colorless crystalline material having an M.P. of 112°–118° C., Yield 0.55 g (14%).

EXAMPLE 52

4-(3,4-Dichlorobenzyl-2-(hexahydro-1-phenethyl-azepin-4-yl)-1-(2H)-phthalazinone 3,36 g (8.35 mmol) of 4-(3,4 dichlorobenzyl)-2-(hexahydro-1H-azepin-4-yl)-1-(2H)-phthalazinone, 4 ml (29.3 mmol) of phenethyl bromide and 4,5 ml (32.20 mmol of triethylamine were dissolved in 20 ml. of dioxane.

The reaction mixture was heated per 12 hours at 100° C. with stirring.

It was rotated, the residue treated with water, eluted with dichloramethane dried with MgS0₄, filtered, concentrated and the resulting oil chromatographed over a silica gel column. The base obtained from the corresponding eluate was converted into the oxalate.

Yield 0.39 g (about 8%) M.P. 161°-162° C.

EXAMPLE 53

4-(4-Methylbenzyl)-2(hexahydro-1-benzylazepin-4-yl)-1-(2H)-phthalazinone

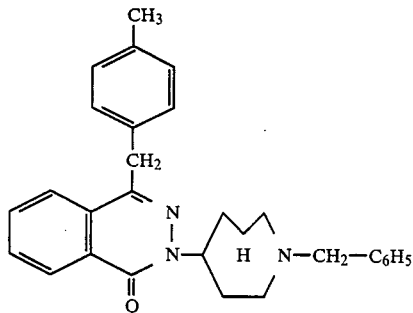

3.02 g (8.69 mmol) of 4-(4-methylbenzyl)-2-(hexahydro-1-H-azepin-4-yl)-1-(2H)-phthalazinone, 3 ml (26.00 mmol) of benzyl chloride and 3.6 ml (25,8 mmol) of triethylamine were dissolved in 20 ml of dioxane.

The reaction mixture was heated for 10 hours with stirring at 100° C. Then the mixture were concentrated, the residue was treated with water and shaken with dichloromethane. The solution was dried with MgSO₄, filtered and concentrated. The oily residue was chromatographed over a silica gel column.

After concentration of the eluate there resulted a crystalline product which was suspended in ether, triturated and filtered with suction.

Yield: 1 g (26.3%) M.P. 128°-129° C.

EXAMPLE 54

4-(4-Fluoro-benzyl)-2-{1-[3-(3,4,5-trimethoxy-phenylcarbonyl)-propyl-(1)]hexahydroazepin-4-yl)-1-(2H)-phthalazinone There were heated for 15 hours under reflux in a stirred apparatus
- 120 ml dried dioxane
- 11.7 g (0,033 mol) 4-(4fluoro-benzyl)-2-(hexahydro-azepin-4-yl)-1-(2H)-phthalazinone
- 13.7 ml (3×0,033 mol) triethylamine and
- 12.4 g (1.3×0.033 mol) 3-(3,4,5-trimethoxy-phenyl-carbonyl)-propyl chloride.

Then the dioxane was distilled off in a rotary evaporator, the residue stirred with methylene chloride, the thus obtained solution was extracted with water, the methylene chloride solution evaporated in a rotary evaporation and the residue purified over a silica gel column.

The thus obtained product was dissolved in ether and the hydrochloride precipitated with HCl. After recrystallization from 30 ml of isopropanol the hydrochloride melts at 145°-148° C. (Yield 4,2 g).

EXAMPLE 55

4-(Fluoro-benzyl)-2{1-[2-(3-trifluormethylphenyl)-ethyl]-hexahydroazepin-4-yl}-1-(2H)-phthalazinone

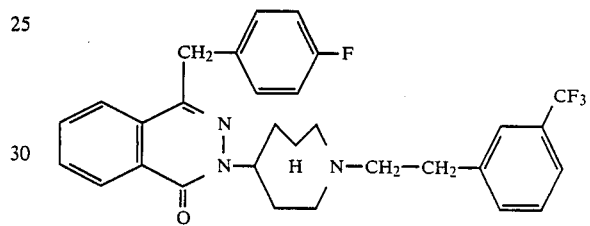

There were added 10.5 g (0,03 mol) of 4-(4-fluoro-benzyl)-2-(hexahydro-azepin-4-yl)-1-(2H)-phthalazinone, 9.1 g of triethylamine and 5 drops of dimethylformamide to 80 ml of dioxane, there were dropped into this mixture at room temperature 10 g (0.04 mol) of 2-[3-trifluoromethyl phenyl]-ethyl bromide and the mixture heated under reflux for 6 hours. After cooling the mixture was filtered with suction. The solution concentrated on a rotary evaporator and dissolved in 150 ml of CHCl₃ and extracted 2 times, each time with 50 ml of water. The CHCl₃ phase was dried over MgSO₄; filtered off and concentrated. The residue was triturated with ether, allowed to stand overnight, filtered with suction, post washed with ether and dried in a vacuum at 40° C. The hydrochloride was produced in isopropanol with an ether solution of hydrochloride acid and the hydrochloride recrystallized from 40 times the amount of acetone. The hydrochloride milled at 184–187° C. (Yield 6.1 g).

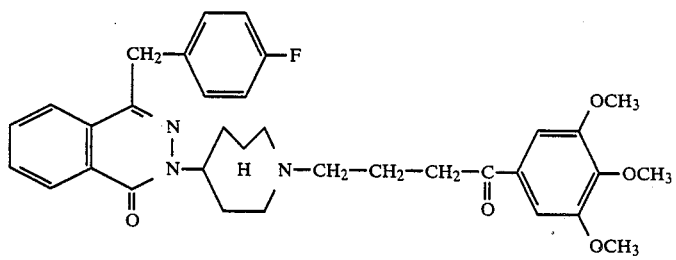

EXAMPLES FOR THE PREPARATION OF PHARMACEUTICAL PREPARATIONS

Tablets, 5 mg active ingredient 50 g of the active ingredient according to Example 5, 450 g lactose, 150 g maize starch and 10 g highly purified amorphous silicon dioxide (silica) are passed through a sieve (mesh size 0.8 mm), mixed and granulated with 200 g of a 5% aqueous gelatine solution in a vortex mixer. The dry granulate, 242 g microcrystalline cellulose, 80 g maize starch and 8 g magnesium stearate are passed through a sieve (0.8 mm mesh size), mixed homogenously and made up by pressing into a tablet in a conventional manner having a weight of 100 mg and a diameter of 6 mm. 1 tablet contains 5 mg active ingredient.

Capsules, 5 mg active ingredient 50 g active ingredient according to Example 7, 50 g maize starch, 1070 g calciumbiphosphatedihydrate and 10 g highly purified, amorphous silicon dioxide are passed through a sieve (0.8 mm mesh size), homogenized and granulated in a vortex mixer with 200 g of 10% aqueous gelatine solution. 200 g Maize starch and the dry granulate are passed through a sieve (0.8 mm mesh size), homogenized and dosed in a conventional manner into 140 mg hard gelatine capsules size 3. 1 capsule contains 5 mg active ingredient.

Water-in-oil cream, 1% active ingredient 10 g micronized active ingredient according to Example 5 are added to a melt (70° C.) from 250 mg white Vaseline. 20 g of an emulsifier made up of fatty acid monoesters of glycerine or of ether polyhydric alcohols (Lunacera alba), 5 g cetyl alcohol and 30 g of a nonionic emulsifier (Cremophor ® water-in-oil-7) with the aid of a highspeed dispersing apparatus. 10 g phenoxyethanol, 20 g glycerine and 655 g water are added to this melt at 70° C. by means of a high-speed emulsifying apparatus and the emulsion is cooled to 30° C. with stirring.

1 g cream contains 10 mg active ingredient.

Oil-in-water cream, 1% active ingredient 10 g micronized active ingredient according to Example 7 are 15 suspended in 100 g low-viscosity paraffin and made up into a melt (70° C.) made up of 60 g polyoxyethanol polyol fatty acid ester, 20 g of a mixture of cetyl alcohol and stearyl alcohol (1:1), 40 g stearic acid and 55 g of a solubilizing agent made up of a mixture of triglycerides of saturated plant fatty acids $C_8$, $C_{10}$ and $C_{12}$ (Miglyol ® 812). The aqueous phase is made up of 10 g phenoxyethanol, 30 g glycerine, 655 g water and 20 g 1N-sodium hydroxide. The two phases are mixed at 60° C. with the aid of a high-speed dispersing apparatus emulsified and stirred until cold. 1 g cream contains 10 mg active ingredient.

The compounds of the present invention display good asthma prophylactic and antiallergic activity in allergic (ovalbumin) asthma in wake guinea pigs. For example, using the above set out test methods at a dose of 0.5 mg/kg body weight in guinea pig brings about a 50% protection against allergically-induced asthmatic attacks.

The lowest dosage found to be active in the above mentioned animal tests is, for example, 0.1 mg/kg by the oral route. As a general dosage range giving rise to activity (animal tests as above) one may, for example, use 0.01-3 mg/kg by the oral route and especially 0.1-1 mg/kg.

The general activity of the compounds according to the present invention is comparable to the activity of the known compound disodium chromoglycinic acid, but the following special differences exist: good peroral activity; leucotriene $C_4$ antagonism.

Indications for the compounds of the present invention which may be considered include: prophylactic treatment of bronchial asthma.

Contraindications: none.

The pharmaceutical formulations contain in general between 0.1–30, preferably 0.5–10 mg, especially 1–5 mg, of the active components according to the present invention.

Administration may for example, take place in the form of tablets, capsules, pills, dragees, suppositories, ointments, gels, creams powders, dusting powders, aerosols or in liquid form. Liquid formulations which may, for example, be used include oily or alcoholic or aqueous solutions as well as suspensions and emulsions. Preferred forms of administration are tablets which contain between 0.5 and 10 mg or solutions which contain from 0.01–5% active substance.

Individual doses of the active components of the present invention may, for example, be the following:

(a) for oral medicaments between 0.5–10 mg, preferably 1–3 mg;

(b) for parenteral medicaments (for example intravenous or intramuscular) between 0.5–3 mg, preferably 0.1–1 mg;

(c) for medicaments for inhalation (solutions or aerosols) between 0.1–2 mg, preferably 0.5–1 mg;

(d) for medicaments for rectal or vaginal application between 0.1–10 mg. preferably 0.5–5 mg:

(e) for medicaments for local application on the skin and mucous membrane (for example in the form of solutions, lotions, emulsions, ointments, etc.) between 1–10 mg, preferably 0.5–5 mg.

The dosage forms are in each case calculated with reference to the free base.

It is, for example, possible to use a 3 times daily dose of 1 to 3 tablets containing from 0.5–5 mg active ingredient or, for example, by intravenous injection 1 to 3 times daily an ampoule containing from 1 to 5 ml with 1 to 5 mg of substance. For oral administration the minimum daily dosage is, for example, 0.5 mg: the maximum daily dose on oral administration should not exceed 50 mg.

For the treatment of dogs and cats the oral single dose is, in general, between 0.03 and 5 mg/kg body weight: the parenteral dosage is generally between about 0.01 and 3 mg/kg body weight.

For the treatment of horses and bovines the oral individual dosage is generally between about 0.03 and 5 mg/kg; the parenteral individual dose is between about 0.01 and 3 mg/kg body weight.

The acute toxicity of the compounds according to the present invention in mice (expresses by the LD 50 mg/kg; method according to Miller and Tainter: Proc. Soc. Exper. Biol. a. Med. 57 (1944) 261) may, for example, lie on oral administration between 500 and 1000 mg/kg.

The medicaments may be used in human medicine, veterinary medicine as well as in agriculture alone or in admixture with other pharmacologically active substances.

They can be used to treat dogs, cats, horses, cattle and sheep for example.

What is claimed:

1. A 4-benzyl-1-(2H)-phthalazinone derivative of the formula

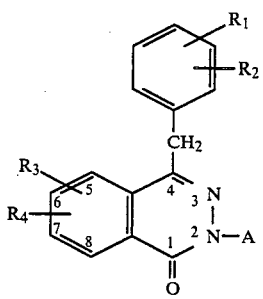

wherein $R_1$ represents fluorine, chlorine, bromine, trifluoromethyl, $C_1$-$C_6$-alkyl, hydroxy, $C_1$-$C_6$-alkoxy, $C_2$-$C_6$-alkanoyloxy, amino, $C_1$-$C_6$-alkylamino, di-$C_1$-$C_6$-alkylamino, $C_2$-$C_6$-alkanoylamino, $C_2$-$C_6$alkanoyl-$C_1$-$C_6$-alkylamino or a nitro group, $R_2$ represents hydrogen or has one of the meanings given above for $R_1$, and $R_1$ and $R_2$ may be the same or different, $R_3$ and $R_4$ may be the same or different and represent hydrogen, halogen, $C_1$-$C_6$-alkyl, hydroxy, $C_1$-$C_6$-alkoxy, benzyloxy or $C_2$-$C_6$-alkanolyloxy and A represents one of the radicals

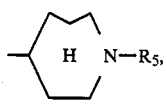

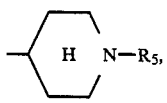

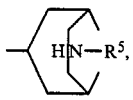

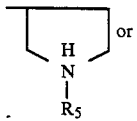

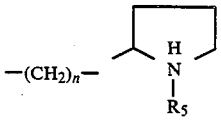

wherein n=1 or 2 and $R_5$ represents a $C_1$-$C_6$-alkyl group substituted by the following radicals:

(a) a phenyl radical or a phenyl carbonyl radical each of which may contain one, two or three substituents, which may be the same or different, whereby the substituents are halogen atoms, trifluoromethyl, $C_1$-$C_6$-alkoxy groups, or (b) a $C_1$-$C_6$-alkoxy radical, a mono or dihydroxy-$C_1$-$C_6$-alkyl radical or a hydroxy-$C_1$-$C_6$ alkoxy radical or (c) a mono-$C_1$-$C_6$-alkylamino or di-$C_1$-$C_6$-alkylamino radical whereby the latter may also be closed to form a 5-7 membered, nitrogen-containing ring, which may optionally contain a further oxygen atom, or (d) a $C_3$-$C_8$-cycloalkyl radical or a $C_3$-$C_8$-cycloalkylcarbonyl radical or wherein $R_5$ is a monounsaturated $C_3$-$C_6$alkyl group, a monounsaturated $C_3$-$C_6$-alkyl group with a phenyl radical, a monounsaturated $C_3$-$C_6$-alkylcarbonyl group or a monounsaturated $C_3$-$C_6$alkylcarbonyl group with a phenyl radical and physiologically acceptable addition salts thereof, with the exception of compounds wherein A represents the radical

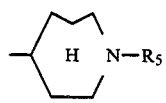

and $R_5$ represents allyl, benzyl, phenylethyl or methoxyethyl, $R_1$ represents chlorine in the 4-position and $R_2$, $R_3$ and $R_4$ represent hydrogen.

2. A compound according to claim 1 wherein $R_2$, $R_3$ and $R_4$ are hydrogen, $R_1$ is fluorine, chlorine or bromine, A is the hexahydroazepin-4-yl group or the piperidyl-(4)-group, $R_5$ is a $C_1$-$C_6$ alkyl group which is substituted by a phenyl group or a phenyl carbonyl group each of which may contain substituents.

3. A compound according to claim 2 wherein $R_1$ is in the 4-position, $R_5$ is methyl, ethyl, propyl or isopropyl substituted in the ω-position.

4. A compound according to claim 3 where $R_1$ is fluorine.

5. A 4-benzyl -1-(2H)-phthalazinone derivative of the formula

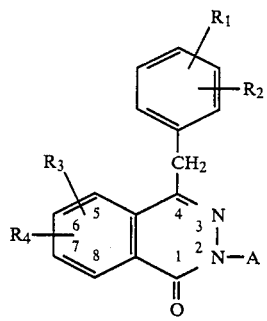

wherein $R_1$ represents fluorine, chlorine, bromine, trifluoromethyl, $c_1$-$C_6$-alkyl, hydroxy, $C_1$-$C_6$-alkoxy, $C_2$-$C_6$-alkanoyloxy, amino, $C_1$-$C_6$-alkylamino, di-$C_1$-$C_6$-alkylamino, $C_2$-$C_6$-alkanoylamino, $C_2$-$C_6$alkanoyl-$C_1$-$C_6$-alkylamino or a nitro group, $R_2$ represents hydrogen or has one of the meanings given above for $R_1$, and $R_1$ and $R_2$ may be the same or different, $R_3$ and $R_4$ may be the same or different and represent hydrogen, halogen, $C_1$-$C_6$-alkyl, hydroxy, $C_1$-$C_6$-alkoxy, benzyloxy or $C_2$-$C_6$-alkanolyloxy and A represents one of the radicals

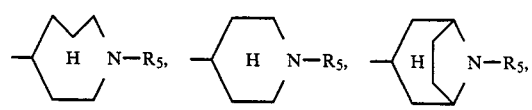

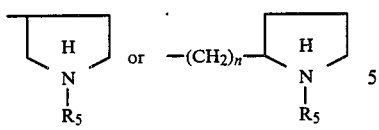

or $-(CH_2)_n-$ 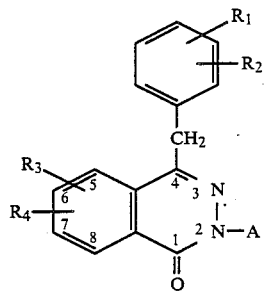

wherein n=1 or 2 and $R_5$ represents a $C_1$-$C_6$-alkyl group substituted by a substituted phenyl radical or a phenyl carbonyl radical wherein the substituent is a $C_1$-$C_4$-alkyl group, a halogen or a $CF_3$ group in the 3-position or three $C_1$-$C_4$-alkoxy groups in the 3, 4 and 5 positions and physiologically acceptable addition salts thereof.

6. A compound according to claim 5 wherein $R_5$ is a substituted phenyl or phenylcarbonyl group wherein the substituent is a methyl group, Cl, F or a $CF_3$ group in the 3-position or three methoxy groups in the 3, 4 and 5-positions.

7. A 4-benzyl-1-(2H)-phthalazinone derivative of the formula wherein $R_1$ is in the 4-position and represents fluorine in the 4-position, $R_2$, $R_3$ and $R_4$ represent hydrogen and A is the hexahydroazepin-4-yl group or the piperidyl-(4)-group which is substitued by a phenylmethyl, phenylethyl, 3-phenyl-propyl, 2-phenylpropyl(1) or phenyl-carbonylmethyl group.

8. A compound according to claim 7 wherein A is hexahydroazepin-4-yl.

* * * * *